United States Patent [19]
Kayser

[11] Patent Number: 6,053,321
[45] Date of Patent: Apr. 25, 2000

[54] BLISTER PACK DISPLAY CARD WITH REUSABLE CONTAINER

[76] Inventor: Steven L. Kayser, 4111 Rander St., San Diego, Calif. 92103

[21] Appl. No.: 09/354,997

[22] Filed: Jul. 16, 1999

Related U.S. Application Data

[60] Provisional application No. 60/093,265, Jul. 17, 1998.

[51] Int. Cl.[7] .................. B65D 73/00; A61B 19/02
[52] U.S. Cl. .................. 206/470; 206/806; 206/807; 206/63.5
[58] Field of Search ................... 206/470, 467, 206/806, 807, 63.5

[56] References Cited

U.S. PATENT DOCUMENTS

| | | | |
|---|---|---|---|
| Re. 33,191 | 4/1990 | Matney | 206/470 |
| 3,111,220 | 11/1963 | Bostrom | 206/470 X |
| 3,463,309 | 8/1969 | Szostek | 206/470 |
| 3,835,224 | 9/1974 | Peters | 206/467 X |
| 4,499,353 | 2/1985 | Shields | 206/470 |
| 4,687,129 | 8/1987 | Cugley | 206/470 X |
| 4,724,964 | 2/1988 | Herrandez | 206/461 |

*Primary Examiner*—Bryon P. Gehman
*Attorney, Agent, or Firm*—Higgs Fletcher & Mack LLP; Bernard L. Kleinke

[57] ABSTRACT

The blister pack has a reusable container mounted to a display card in a tamper resistant manner. The reusable container has a tray and a lid with the tray having frangible flanges thereon which are sealed to a presentation side of the display card. The lid has a deep channel which is received frictionally into the tray for securely closing the reusable container. Both the lid and the tray have enlarged finger engageable pull tabs for ease of opening the reusable container.

18 Claims, 1 Drawing Sheet

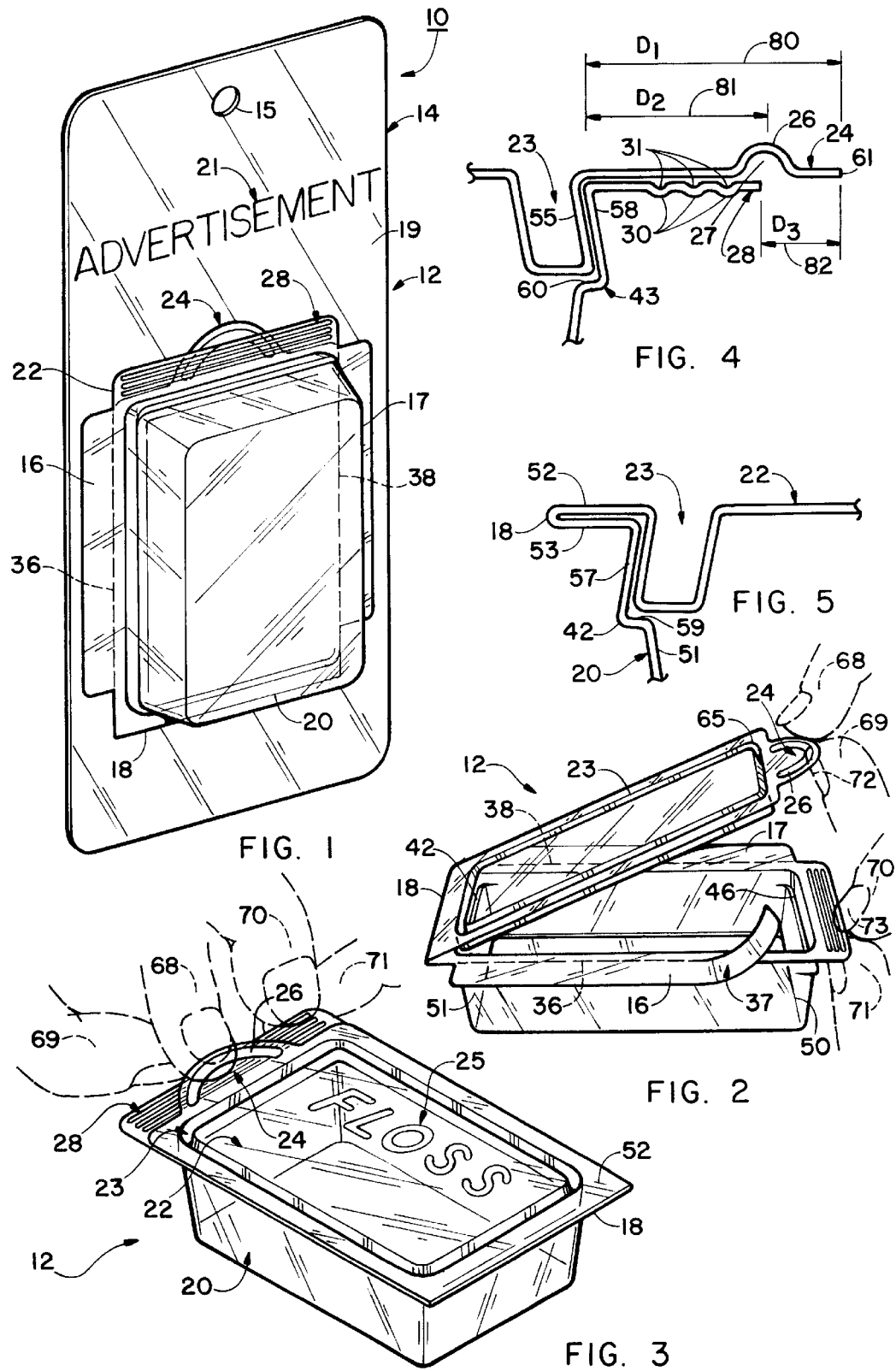

6,053,321

BLISTER PACK DISPLAY CARD WITH REUSABLE CONTAINER

CROSS-REFERENCE TO RELATED APPLICATIONS

This application claims the benefit of U. S. Provisional Application No. 60/093,265 filed Jul. 17, 1998 and entitled "DISPLAY-CARD AVULSABLE & REUSABLE PLASTIC-CONTAINER," which is incorporated herein by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Technical Field

The field of the present invention is display packaging. More specifically, the field relates to providing a blister pack having a reusable container on a display card.

2. Background Art

In the retail store environment it is necessary to conveniently and attractively display items for sale. In particular, when selling a quantity of small items, it is often necessary to place the numerous small items in a single container. For convenient display it is desirable that a customer be able to see the numerous small items prior to purchase. Therefore, others have provided substantially transparent packaging attached to display cards in the form of reusable blister packs.

For example, U.S. Pat. No. 4,724,964 discloses a reusable plastic container mounted to a backing board wherein numerous items such as screws are placed in the plastic container and the plastic container is mounted to a backing board. In such a manner, after purchase the customer may remove the plastic container from the backing board and continue to use the plastic container as the holding device for the screws.

However, some items require a higher degree of tamper resistance. For example, selling items related to the dental or medical field requires that the medical or dental items be protected against tampering. For example, the sale of multiple small flossing devices need a package for attractively and conveniently displaying the flossing items. However, the packaging must be highly tamper resistant, as the flossing device is intended to be placed in the mouth of the customer. Known prior art display systems do not provide a level of tamper resistance sufficient to assure customers that the product they are buying is safe. Thereby, there exists a need for an attractive packaging for displaying small items needing a high degree of tamper resistance.

Another problem with storing medical or dental items is that the items must be safely and securely stored so the items do not spill from the container. For example, if the flossing devices discussed above spill from their container and fall to the floor, the flossing devices must be thrown out as they are now unsanitary. However, if the container is constructed such that the lid and tray of the container mate in a tight frictional fit to avoid accidental spillage, then the container becomes difficult to open. In particular, elderly or those with dexterity limitations, such as those suffering from arthritis, will be unable to open the container.

Further, when a person grasps the tray of the container and forcefully pulls open the lid, it is highly likely that items within the tray will "pop out" and thereby be contaminated. Thus, although it is highly desirable to have containers that are securely closed, such containers are difficult for many to open, and when opened, often spill their contents anyway. Therefore, there exists a need for a reusable container that is closeable in a secure manner but yet allows for ease of opening.

SUMMARY OF THE INVENTION

It is therefore an object of the present invention to provide a blister pack in the form of a display card and a reusable container that safely and attractively allows the display of items with a high degree of tamper resistance.

It is a further object of the present invention to provide a reusable plastic container for a blister pack that is securely closeable but which can be easily opened without spilling the contents therein.

To overcome the deficiencies in the prior art and to meet the above objectives, herein is provided a novel display card with reusable container in the form of a blister pack. The blister pack has a reusable container mounted to a display card in a tamper resistant manner. The reusable container has a tray and a lid with the tray having frangible flanges thereon which are sealed to a presentation side of the display card. The lid has a deep channel which is received frictionally into the tray for securely closing the reusable container. Both the lid and the tray have enlarged finger engageable pull tabs for ease of opening the reusable container.

Since the tray is heat sealed to the presentation side of the display card, any attempt to remove the tray from the display card will be evident as the surface of the display card will be damaged. In such a manner, any customer approaching the display card will immediately know if another has attempted to open and contaminate the displayed product. After a customer purchases an unadulterated package, the customer engages the pull tab on the lid to easily remove the reusable container from the display card. The display card and frangible flanges are discarded leaving a convenient reusable plastic container. Since the lid has a deep channel frictionally received by the tray, the plastic container is securely and safely closed. However, the customer can still easily open the plastic container as both the lid and the tray each have an enlarged finger engageable tab. In such a manner the customer engages the tray pull tab with the finger and thumb of one hand while engaging the lid pull tab with the finger and thumb of the other hand. The customer thereby easily and smoothly opens the reusable container.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIG. 1 is a pictorial illustration of a blister pack made in accordance with the present invention that includes a display card and a reusable container;

FIG. 2 is a pictorial perspective view of the reusable container of FIG. 1 removed from the display card with the lid shown in a partially opened position;

FIG. 3 is a pictorial side view of the reusable container of FIG. 2 with the frangible flanges removed and the lid in a closed position;

FIG. 4 is an enlarged cross-sectional view of pull tabs of the reusable container made in accordance with the present invention; and FIG. 5 is an enlarged cross-sectional view of the hinge of the reusable container made in accordance with the present invention.

BEST MODE FOR CARRYING OUT THE INVENTION

Referring to FIG. 1 there is shown a blister pack 10 made in accordance with the present invention. The blister pack 10 generally comprises a display card 14 with a reusable container 12 attached thereto. The reusable container 12 has a tray 20 having frangible flanges 16 and 17. The frangible flanges 16 and 17 are securely heat sealed to the display card 14. In such a manner, when the reusable container 12 is removed from the display card 14, the surface material on the display card 14 is torn or degraded in an obvious manner. Thereby, any attempt to open the removable container 12 or remove the reusable container 12 from the display card 14 is immediately obvious.

In use, blister pack 10 is positioned on a retail display rack for view and selection by customers. A customer may view multiple items held within the reusable container 12 as the reusable container 12 is constructed from a substantially transparent plastic material. As any attempt to remove the reusable container 12 from the display card 14 results in an obvious deformation to the display card, a customer selects a blister pack 10 that has not been tampered with. After purchasing a blister pack 10, the customer grasps an enlarged pull tab on the lid to pull the reusable container 12 away from the display card 14. As the reusable container 12 is removed from the display card 14, the frangible flanges 16 and 17 tear the presentation surface 19 of the display card 14. After removing the reusable container 12 from the display card 14, the customer breaks the frangible flanges 16 and 17 from the reusable container 12.

Although the lid 22 is securely frictionally engaged to the tray 20 of the reusable container 12, the customer can easily and smoothly open the reusable container 12. In such a manner, the customer uses the thumb and forefinger of one hand to engage the enlarged pull tab on the lid and uses the thumb and forefinger on the other hand to engage the elongated pull tab on the tray. By pulling the pull tabs apart, the lid 22 can be smoothly disengaged from the tray 20. Thereby, the reusable container 12 is opened in a smooth manner without spilling the contents of the tray 20.

With the blister pack 10 generally described, components parts will now be described in more detail The display card 14 is a planar card constructed from a common material such as paper, plastic or cardboard. The display card 14 has a presentation surface 19 intended to be viewed by a retail customers. For example, the display card 14 may be positioned on rack hooks using display hole 15. In such a manner, the hook from the rack is inserted through the display hole 15 with the presentation side 19 of the display card 14 displayed to customers. The presentation side 19 may have advertising such as indicia 21 for identifying the product to customers. Other colorations, designs, and materials may be used on the presentation side 19. As will be further described, the display card 14 is constructed such that the presentation side 19 tears or deforms under stress.

Referring now to FIGS. 1–3, the reusable container 12 will be described in more detail. Reusable container 12 is constructed from a plastic material such as a PVC thermoplastic. Those skilled in the art will recognize other materials can be substituted. In a preferred embodiment, the reusable container 12 is substantially transparent thereby allowing customers to view the contents of the reusable container 12. Those skilled in the art will recognize other plastics and finishes can be readily substituted. The reusable container 12 is also preferably constructed from a single plastic piece by a molding or stamping process. Such molding and stamping manufacturing processes are well-known by those skilled in the art. Alternatively, the reusable container 12 can be constructed from discreet parts.

The reusable container 12 is a closable box. The reusable container 12 generally includes a tray 20 and a lid 22. The tray 20 has a bottom, left and right side walls, a front wall, and a back wall.

The reusable container 12 also has a lid 22. The lid 22 is constructed to engage the rim of the tray in a substantially flat manner. The lid 22 has a deep channel 23 extending completely around the lid's periphery. This deep channel 23 of the lid 22 frictionally engages the walls of the tray 20.

A living hinge 18 integrally connects the lid 22 hingedly to the tray 20. The hinge 18, as detailed in FIG. 5, is generally "U" shaped and constructed as a single creased hinge. Such a single creased hinge 18 enables the lid 22 to engage the rim of the tray 20 in a substantially flush manner. In such a manner, the reusable container 12 may be more easily and securely sealed to the display card 14. Further, the hinge 18 is offset from the back wall 51 of the tray 20. Thereby, the hinge 18 includes a bottom hinge flange 53 and a top hinge flange 52. The top hinge flange 52 and the top hinge flange 53 position the hinge 18 offset from the tray 20. Such an offset further facilitates a smooth and secure frictional engagement of the lid 22 into the tray 20.

As shown in FIGS. 4 and 5, the channel 23 of the lid 22 has an outer channel wall 55 for engaging the front tray wall 50 and the back tray wall 51. The back tray wall 51 has a ledge wall 57 extending from the bottom hinge flange 53. The ledge wall 57 has a negative angle for frictionally receiving the back channel wall 55. Thus, as the lid 22 rotates about hinge 18, the back channel wall 55 is pulled into increasing frictional contact with the ledge wall 57. In such a manner the lid 22 is locked to the tray so that the lid 22 can not be lifted straight out of the tray. Thereby the lid 22 is more securely coupled to the tray 20. As the lid 22 is further brought into the tray 20, the channel 23 is brought proximately the hinge tray ledge 42. The hinge tray ledge 42 has a ledge surface 59 which may contact the deep channel 23.

The lid 22 has an interference fit with the tray 20 for assuring the lid is securely retained in the tray. Referring now to FIG. 4, the channel 23 is shown engaging the front tray wall 50. In a manner similar to that described above, the channel wall 55 engages the negatively sloped ledge wall 58. As the lid is further closed to the tray, the channel 23 is brought proximate the tray ledge 43. As the lid 22 becomes fully closed to the tray 20, the lid channel 23 may bottom with the ledge surface 60. Due to the deep channel 23 and the negative engagement provided by the tray walls, the lid is very securely frictionally engaged to the tray 20.

Referring now to FIG. 2 there is shown the tray 20 having frangible flanges 16 and 17. These frangible flanges 16 and 17 attach to tray 20 through perforations 36 and 38. In such a manner, a customer can easily and conveniently remove frangible flanges 16 and 17 after the reusable container 12 has been removed from its display card. Referring again to FIG. 1, it can be seen that the frangible flanges 16 and 17 are securely heat sealed to the display card 14. As described above, the lid is securely and flatly closed to the tray 20. In such a manner, the closed reusable container 12 is securely attached to display card 14.

Referring again to FIG. 2, the reusable container 12 is shown removed from the display card 14. Frangible flange 16 is shown with part of the frangible flange 16 being removed at reference character 37. Referring now to FIG. 3, the reusable container 12 is shown with the frangible flanges 16 and 17 entirely removed.

The lid 22 of the reusable container 12 has an enlarged lid pull tab 24 for engaging the finger/thumb of a customer. For example, to remove the reusable container 12 from the display card 14, a customer moves a finger or another device such as a knife between the lid pull tab 24 and the presentation surface 19 of the display card 14. As the finger or other device is pried between the reusable container 12 and the display card 14, the reusable container 12 moves away from the display card 14. As the reusable container 12 moves away, the frangible flanges 16 and 17 tear away from the display care 14 until the reusable container 12 is completely separated. In such a manner, the enlarged lid pull tab 24 facilitates the easy removal of the reusable container 12 from the display card 14.

The lid pull tab 24 extends from the front of the lid 22 and is generally curvilinear in shape. The lid pull tab 24 also is substantially narrower than the width of the tray and is centrally located relative to the width of the tray 20. However, the lid pull tab 24 may be positioned in other locations on the lid as recognized by those skilled in the art. The enlarged lid pull tab 24 also has a substantial ridge 26. The substantial ridge 26 generally follows the curved periphery of the lid pull tab 24. Positioned opposite ridge 26 is groove 27. Groove 27 is constructed for receiving a finger nail Those skilled in the art will recognize other types of ridges or grooves may be substituted. Such a substantial ridge and groove further assists in the user engaging the pull tab 24 when removing the reusable container 12 from the display card 14.

The substantial ridge 26 is generally crescent shaped and facilitates the effective sealing of the frangible flanges 17 and 18 to the display card 14. During the manufacturing process, the substantial ridge 26 prevents the display card 14 from curling forward after heat sealing and causing the reusable container 10 to not be flush mounted.

The tray 22 has a tray pull tab 28 for engaging the thumb and fingers of a user. The tray pull tab extends from the front wall of the tray 22 and is constructed substantially as wide as the tray 22. The tray pull tab 28 has a plurality of pull tab ridges in its surface. These ridges assist in engaging the thumb and fingers of a user. Positioned opposite the ridges 30 are grooves 31. Grooves 31 are constructed to receive a finger nail.

The lid pull tab 24 extends away from the tray front wall 50 by a distance $D_1$ 80 as shown in FIG. 4. The tray pull tab 28 extends from the tray front wall 50 by a distance $D_2$ 81. Thereby, the lid pull tab 24 overhangs the tray pull tab by a distance $D_3$ 82. In such a manner a user is able to easily place a right hand thumb 69 into the overhang area 82 and oppositely place a right hand forefinger 68 on the substantial ridge 26. Further, the right thumb nail 72 may be received into the groove 27 to assist in engaging the lid pull tab 24. Thus, the user is able easily to lift and slightly bend the lid pull tab 24.

Since the tray pull tab 28 extends the entire width of the tray 22, the user is also easily able to engage the top surface of the tray pull tab 28 with a left hand thumb 70. While placing slight downward pressure on the tray pull tab 28 with the left hand thumb 70, the user oppositely positions a left hand forefinger and engages the tray pull tab ridges 30. Further, the left thumb nail 73 may be received into the groove 31 to assist in engaging the tray pull tab 28. By applying a pulling force between the left hand and the right hand, the lid 22 can be smoothly disengaged from the tray 20.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A tamper resistant blister pack having a reusable container, comprising:
   a planar display card having a presentation surface, the presentation surface obviously deforming under stress;
   a reusable container having a tray and a lid;
   a deep channel in the lid for frictionally engaging walls of the tray so that when closed the lid is securely retained in the tray;
   a hinge connecting the lid to the tray so that when closed the lid is held substantially flushly to a rim of the tray;
   a pair of frangible flanges removably coupled to the tray rim, each of the frangible flanges sealed to the presentation surface of the display card;
   an elongated tray pull tab coupled to the tray front wall and extending substantially the width of the tray, the tray pull tab having a finger engageable area;
   means on the finger engageable area of the tray pull tab for assisting engaging the digits of a user;
   a lid pull tab attached to the lid and extending less than the width of the tray, the lid pull tab having a finger engageable area that extends beyond the finger engageable area of the tray pull tab; and
   a substantial ridge in the finger engageable area of the lid pull tab.

2. The tamper resistant blister pack according to claim 1 wherein the reusable container is constructed from a single piece.

3. The tamper resistant blister pack according to claim 1 wherein the hinge is a single crease hinge.

4. The tamper resistant blister pack according to claim 1 wherein the lid has a tight interference fit with the tray.

5. The tamper resistant blister pack according to claim 1 further including means for defining a thumb nail engaging groove on the lid pull tab.

6. The tamper resistant blister pack according to claim 1 further including means for defining a thumb nail engaging groove on the tray pull tab.

7. A reusable plastic container for use on a blister pack, comprising:
   a tray constructed in a generally rectangular shape and having a front wall, a hinge wall, and side walls, the front wall being substantially longer than each side wall;
   a lid constructed to flushly engage a rim of the tray peripheral rim;
   a deep channel in the lid for frictionally engaging walls of the tray so that when closed the lid is securely retained in the tray;
   an offset hinge connecting the lid to the tray so that when closed the lid is held substantially flushly to the tray rim;

a pair of frangible flanges removably coupled to the tray rim, each of the frangible flanges for sealing to a display card;

an elongated tray pull tab coupled to the tray front wall and extending substantially the width of the tray, the tray pull tab having a finger engageable area;

means on the finger engageable area of the tray pull tab for assisting engaging the digits of a user;

a lid pull tab attached to the lid and extending less than the width of the lid, the tray pull tab having a finger engageable area that extends beyond the finger engageable area of the tray pull tab; and a substantial ridge in the finger engageable area of the lid pull tab.

8. The reusable plastic container according to claim 7 wherein the reusable container is constructed from a single piece.

9. The reusable plastic container according to claim 7 wherein the hinge is a single crease hinge.

10. The reusable plastic container according to claim 7 wherein the lid has a tight interference fit with the tray.

11. The reusable plastic container according to claim 7 further including means for defining a thumb nail engaging groove on the lid pull tab.

12. The reusable plastic container according to claim 7 further including means for defining a thumb nail engaging groove on the tray pull tab.

13. A method of making a reusable plastic container for use on a blister pack, comprising:

constructing a tray in a generally rectangular shape, the tray having a front wall, a hinge wall and side walls, the front wall being substantially longer than each side wall;

constructing a lid to flushly engage a peripheral rim of the tray;

forming a deep channel in the lid for frictionally engaging walls of the tray so that when closed the lid is securely retained in the tray;

offsetting a hinge between the lid and the tray, the hinge for connecting the lid to the tray so that when closed the lid is held substantially flushly to the tray rim;

perforating a pair of removable frangible flanges on the tray rim, each of the frangible flanges for sealing to a display card;

forming an elongated tray pull tab, the tray pull tab being coupled to the tray front wall and extending substantially the width of the tray, the tray pull tab having a finger engageable area;

defining means on the finger engageable area of the tray pull tab for assisting engaging the digits of a user;

forming a lid pull tab, the lid pull tab being attached to the lid and extending less than the width of the tray, the lid pull tab having a finger engageable area that extends beyond the finger engageable area of the tray pull tab; and defining a substantial ridge in the finger engageable area of the lid pull tab.

14. The method of making a reusable plastic container according to claim 13 including constructing the reusable container from a single piece.

15. The method of making a reusable plastic container according to claim 13 further including pressing a single crease to form the hinge.

16. The method of making a reusable plastic container according to claim 13 further including defining a thumb nail engaging groove on the lid pull tab.

17. The method of making a reusable plastic container according to claim 13 further including defining a thumb nail engaging groove on the tray pull tab.

18. A method of using a blister pack that includes a reusable plastic container and a display card, the reusable container having a lid hinged to a tray, with the tray being sealed to the display card, comprising:

engaging a lid pull tab, the lid pull tab being attached to the lid of the reusable plastic container and positioned substantially flush with the display card;

prying, using the lid pull tab, the reusable plastic container from the display card;

removing a pair of perforated frangible flanges from the tray;

engaging, with a thumb nail, a nail groove in the lid pull tab;

pressing a finger on the lid pull tab, the finger positioned opposite the thumb nail so that one hand securely holds the lid pull tab;

engaging, with another thumb nail, a nail groove in a tray pull tab;

pressing another finger on the tray pull tab, the another finger positioned opposite the another thumb nail, so that another hand securely holds the tray pull tab; and pulling the one hand away from the another hand so that the lid is pivotly disengaged from the tray in a smooth manner.

* * * * *